United States Patent [19]

Kubo et al.

[11] Patent Number: 4,560,554

[45] Date of Patent: Dec. 24, 1985

[54] NEUTRALIZER FOR COLD WAVING

[75] Inventors: Sanae Kubo, Sagamihara; Emiko Kawada, Yokohama, both of Japan

[73] Assignee: Shiseido Company Ltd., Tokyo, Japan

[21] Appl. No.: 596,225

[22] Filed: Apr. 3, 1984

[30] Foreign Application Priority Data

Sep. 20, 1983 [JP] Japan ................................ 58-173396

[51] Int. Cl.[4] .......................... A61K 7/09; A61K 7/11; A61K 7/35
[52] U.S. Cl. ....................................... 424/71; 424/72; 424/62
[58] Field of Search ............................. 424/71, 72, 62

[56] References Cited

U.S. PATENT DOCUMENTS 3,988,110 10/1976 Zviak et al. .................. 424/DIG. 2
4,358,286 11/1982 Grollier et al. ........................ 424/74
4,424,379 1/1984 Sprecker et al. ....................... 424/49

OTHER PUBLICATIONS

Sagarin, *Cosmetics Science & Technology*, pp. 634–635 (1957).
Merck, 9th Ed., p. 239 (abst. 1867) (1976).

*Primary Examiner*—Albert T. Meyers
*Assistant Examiner*—F. Abramson
*Attorney, Agent, or Firm*—Sprung, Horn, Kramer & Woods

[57] ABSTRACT

A neutralizer for cold waving comprising: (i) an oxidizing agent and (ii) at least one compound selected from the group consisting of the compounds having the general formula (I) to (XII), as follows.

(Abstract continued on next page.)

wherein —$R_1$ and —$R_2$ are independently —$CH_3$, —$CH_2OH$, —$CH_2Cl$, —$CH_2Br$, —$CH_2I$, and

, —$CH_2CO$—,

—$CH_2COOR_6$, —$CH_2CH_2COOR_6$, —$CH_2COR_6$, —$COR_6$,

—$R_3$, —$R_4$, and —$R_5$ are independently —H, —$COR_6$, —$COOR_6$, —Cl, —Br, —I, —$NO_2$, —$OCH_3$, —OH, and —COOH;

—$R_6$ is hydrogen atom, or an alkyl or alkenyl group having up to 3 carbon atoms;

—$R_7$ is —H, —OH, or —$CH_3$; and

—$R_8$ is —H, —$COCH(CH_3)_2$, —$COCH=C(CH_3)_2$, —$COCH_3$, $$-COCH_2\underset{\underset{CH_3}{|}}{C}=C(CH_3)_2, \text{ or } -COCH_2\underset{\underset{OH}{|}}{C}(CH_3)_2.$$

This neutralizer generates no substantial mercaptan or other unpleasant odor when applied to the hair and forms an elastic and shiny permanent wave.

3 Claims, 2 Drawing Figures

Fig. 1

NEUTRALIZER FOR COLD WAVING

BACKGROUND OF THE INVENTION

1. Field of the Invention

The present invention relates to a neutralizer for cold waving. More specifically, it relates to a neutralizer for cold waving which is formulated by incorporating dibenzyl ketone, p-diacetyl benzene, 2-hydroxy-1,4-naphthoquinone, hinokitiol, shikonin, or a similar compound into a conventional neutralizer containing as a main ingredient an oxidizing agent. This neutralizer has the following two characteristics:

(a) An unpleasant odor (e.g., a mercaptan odor) is not substantially generated in the hair when the neutralizer is applied to the hair; and (b) An elastic and shiny wave is formed in the hair.

2. Description of the Prior Art

As is well known in the art, permanent waving lotions are composed of (i) waving lotions containing, as a main component, reducing agents, that is, mercapto compounds such as thioglycolic acid and cysteine, and (ii) neutralizers containing oxidizing agents such as sodium bromate and hydrogen peroxide. However, the use of conventional permanent waving lotions involves a problem in that an extremely unpleasant mercaptan odor is generated in the hair when the permanent waving lotions are applied to the hair. This unpleasant odor specific to the permanent waving lotions cannot be removed from the hair even when the hair is shampooed several times. Thus, the use of conventional permanent waving lotions is not agreeable to consumers.

Various attempts have been made to eliminate the above-mentioned unpleasant mercaptan odor, among which are typical conventional methods for eliminating the unpleasant mercaptan odor employing so-called masking techniques in which perfumes having a strong odor are incorporated into permanent waving lotions, to thereby mask the unpleasant mercaptan odor in the hair.

However, the mercaptan odor still remains in the hair and has a bad or unpleasant odor. Moreover, since the density of gaseous mercaptan is heavier than that of air, the mercaptan odor drifts down from the hair toward the neighborhood of the nose, especially during shampooing or perspiration. Therefore, the mercaptan odor cannot be completely mashed by the perfume odor remaining in the hair. Furthermore, some people dislike the perfumes which are generally used in these masking methods, due to their strong and heavy odor.

For the above-mentioned reasons, it is considered that the mercaptan odor per se must be eliminated in order to fundamentally solve the above-mentioned problems of unpleasant odor.

SUMMARY OF THE INVENTION

Accordingly, the object of the present invention is to fundamentally eliminate the above-mentioned generation of an unpleasant odor from a neutralizer of a permanent waving lotion and to provide a neutralizer generating no substantial mercaptan odor when applied to the hair.

Other objects and advantages of the present invention will be apparent from the following description.

In accordance with the present invention, there is provided a neutralizer for cold waving comprising: (i) an oxidizing agent and (ii) at least one compound selected from the group consisting of the compounds having the general formula (I) to (XII), shown as follows.

wherein —$R_1$ and —$R_2$ are independently —$CH_3$, —$CH_2OH$, —$CH_2Cl$, —$CH_2Br$, —$CH_2I$,

—$CH_2COOR_6$, —$CH_2CH_2COOR_6$, —$CH_2COR_6$, —$COR_6$,

—$R_3$, —$R_4$, and —$R_5$ are independently —H, —$COR_6$, —$COOR_6$, —Cl, —Br, —I, —$NO_2$, —$OCH_3$, —OH, and —COOH;

—$R_6$ is a hydrogen atom, or an alkyl or alkenyl group having up to 3 carbon atoms;

—$R_7$ is —H, —OH, or —$CH_3$; and

—$R_8$ is —H, —$COCH(CH_3)_2$, —$COCH=C(CH_3)_2$, —$COCH_3$,

BRIEF DESCRIPTION OF THE DRAWINGS

The present invention will be better understood from the following descriptions presented in connection with the accompanying drawings in which.

DESCRIPTION OF THE PREFERRED EMBODIMENTS

The compounds (ii) usable in the formulation of the neutralizer according to the present invention are those having the above-mentioned general formulae (I) to (XII). These compounds may be used alone or in any mixture thereof. The preferable compounds are dibenzyl ketone, p-diacetyl benzene, 2-hydroxy-1,4-naphthoquinone, hinokitiol, shikonin, benzyl acetophenone, p-nitroacetophenone, p-hydroxyacetophenone, benzophenone, 2,5-dihydroxy-1,4-benzoquinone, 2-cyclohexenone, carvone, ethyllevulinate.

The compounds (ii) having the above-mentioned general formulae (I) to (XII) are preferably incorporated into the neutralizers according to the present invention in an amount of 0.0001% to 5.0% by weight, more preferably, 0.0005% to 5.0% by weight, based on the total weight of the neutralizers. When the amount of the compounds (ii) in the present neutralizers are less than 0.0001% by weight, the desired odor elimination effect cannot be obtained. Contrary to this, when the amount of the compounds (ii) in the present neutralizers is larger than 5.0% by weight, the compounds (ii) tend to be separated or precipitated so that the stable formulation is difficult, and the odor of the compounds (ii) per se is undesirably generated depending upon the kinds of the compounds (ii).

The neutralizers of the present invention contain, as a main component, any conventional oxidizing agent. Examples of such oxidizing agents are bromates such as sodium bromate and potassium bromate, hydrogen peroxide, sodium percarbonate, and sodium perborate.

These oxidizing agents may be used alone or in any mixture thereof. Although there is no specific limitation in the content of the oxidizing agents in the neutralizer, the oxidizing agents are preferably incorporated into the neutralizer in an amount of 0.5% to 20% by weight, more preferably 1% to 10% by weight, based on the total weight of the neutralizer.

The neutralizer of the present invention may optionally contain any conventional ingredients used in conventional neutralizers, as long as the desired effect of the present invention is not adversely affected. Examples of such conventional ingredients are pH adjusting agents such as potassium phosphate (monobasic, dibasic), sodium phosphate (monobasic, dibasic) oils such as liquid paraffines, squalene, fatty alcohols, triglyceride, esters, silicone oils, and lanolin, surfactants such as nonionic surfactants (e.g., polyoxyethylene alkyl ether), anionic surfactants (e.g., sodium lauryl sulfate, sodium laurate), and cationic surfactants (e.g., stearyl trimethyl ammonium chloride), sequestrants such as ethylene diamine tetra acetate (EDTA), colorants such as Guaiazulene, Quinoline yellow WS (D. & C. Yellow No. 10), Rhodamine B (D. & C. Red No. 19), perfumes, preservatives such as methyl parabene, sodium benzoate, and other agents such as water soluble polymers, cationic polymers, polypeptide, amino acids, and humectants.

The neutralizers of the present invention can be prepared in any conventional manner, with the proviso that the above-mentioned compounds (ii) are included therein. The above-mentioned compounds (ii) can be directly incorporated into the neutralizers. Alternatively, the compounds (ii) are previously solubilized by surfactants. Furthermore, the compounds (ii) are previously dissolved in oils and are then emulsified by surfactants, or are then incorporated into a higher alcohol-surfactant type liquid crystal gel.

The neutralizers according to the present invention may be applied to the hair in the same manner as conventional neutralizers. For example, waving lotions containing, as a main ingredient, reducing agents such as thioglycolic acid, thioglycolates such as sodium thioglycolate, potassium thioglycolate, ammonium thioglycolate, monoethanol amine thioglycolate, glycerol monothioglycolate, thiolactic acid and its salts, and L-Alginine thioglycolate, cysteine, cysteine derivatives such as N-acetyl-L-cysteine, and cysteine ethylester, and salts, such as hydrochloric acid, and sulfuric acid salts, of the cysteine derivatives, are first applied to the hair. After waving the hair, the neutralizers of the hair, the neutralizers of the present invention are applied to the hair. The hair thus treated with the neutralizers was rod out and, then, water rinsed.

EXAMPLE

The present invention now will be further illustrated by, but is by no means limited to, the following examples, in which all percentages and parts are expressed on a weight basis unless otherwise specified.

EXAMPLE 1

(1) A wave lotion and neutralizer were prepared according to the following standard formulations.

| Composition | % |
| --- | --- |
| Waving lotion | |
| 50% Aqueous ammonium thioglycolate | 13.0 |
| 28% Special reagent grade aqueous ammonia | 1.0 |
| Ammonium bicarbonate | 4.0 |
| Tetrasodium EDTA | 0.1 |
| Sodium lauryl sulfate | 0.1 |
| Purified water | balance |
| Neutralizer | |
| Sodium bromate | 6.0 |
| Potassium phosphate, monobasic | 0.4 |
| Disodium phosphate, dibasic | 0.05 |
| Sodium lauryl sulfate | 0.1 |
| Shikonin* | 0.001 |

| Composition | % |
| --- | --- |
| Purified water | balance |

[Chemical structure: naphthoquinone with OH groups and prenyl side chain]

(2) 20% Index

Ten strands of non-damaged hair from the head of a 20 to 29 year old woman were bundled and were dipped in water. The hair was elongated by 20% in the completely wet state and the load ($h_0$) required was measured. After the measurement, the hair was at once dipped in water again and was allowed to stand in the water for a while. The hair was taken out from the water and was allowed to dry naturally for one day in a room temperature. The dried hair was treated with the above-prepared waving lotion at a temperature of 30° C. for 10 minutes and was then washed with water. Thereafter, the hair was treated with the above-mentioned neutralizer at a temperature of 30° C. for 10 minutes, followed by water washing. The hair thus obtained was again elongated by 20% in a completely wet state and the load (h) required was measured.

The 20% index was calculated from the following equation:

$$20\% \text{ Index} = \frac{h}{h_0}$$

The 20% index is a criterion of the recovery of hair strength with a neutralizer. A 20% index of 1.0 means that the hair is completely recovered to the original state. The smaller the 20% index, the weaker the recovery of the hair strength.

(3) Mercaptan generation amount and remaining odor of permanent waved hair after neutralizer is applied A 0.5 g amount of non-damaged hair from the head of a 20 to 29 year old woman was placed in a 100 ml Erlenmeyer flask and 2 ml of the waving lotion was charged thereinto. Thus, the hair was uniformly dipped in the waving lotion. After the flask was stoppered, the hair was treated with the waving lotion at a temperature of 30° C. for 10 minutes, while shaking, in a constant temperature water bath. The hair was then rapidly washed with water and the excess water in the hair was removed by wiping with a towel. The hair was placed in another 100 ml Erlenmeyer flask and was then uniformly dipped in 1 ml of the neutralizer. The flask was plagged at the top thereof with paraffinefilm and the hair was treated with the neutralizer at a temperature of 30° C. for 20 minutes, while stirring, in a constant temperature water bath.

The gas generated in the upper space of the flask was sampled in a volume of 0.5 ml with a gas-tight cyringe every 5 minutes and was quantitatively determined by a gas chromatograph apparatus (GC-FPD). After 20 minutes' treatment, the treated hair was washed with water and the excess water in the washed hair was removed by wiping with a towel. The odor of the hair was organoleptically evaluated immediately after removal of the excess water. The hair was then allowed to stand for one day in a room temperature and the odor of the hair was again organoleptically evaluated while wetting with water.

Figure 1:
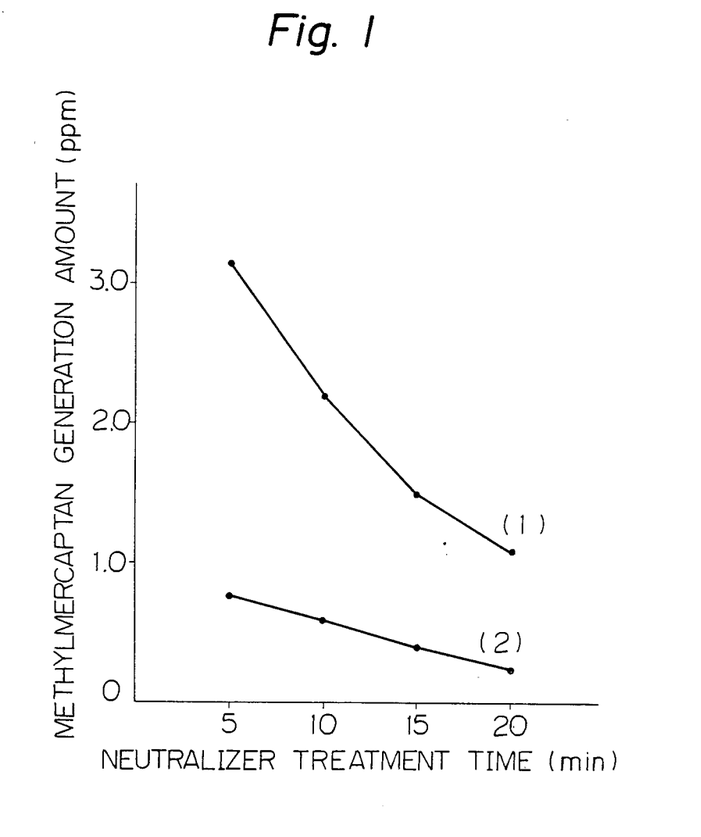
FIG. 1 is a graph illustrating a correlation between a neutralizer treatment time and a methylmercaptan generation amount obtained in Example 1.

The odor was evaluated according to the following criteria:

−−: Strong mercaptan odor
−: Moderately strong mercaptan odor
±: Very weak mercaptan odor
+: No substantial mercaptan odor
++: No mercaptan odor The results of the above-mentioned 20% index, mercaptan generation amount, and remaining mercaptan odor in the permanent wave treated hair are shown in Table 1 and FIG. 1. In FIG. 1, the mercaptan generation amounts in Table 1 are shown graphically, in which curve (1) represents the case where no shikonin was included in the neutralizer and curve (2) represents the case where 0.001% of shikonin was included.

TABLE 1

Methylmercaptan generation amount, remaining odor, and 20% index when treated with neutralizer

| Amount of compound (ii) in neutralizer | Treatment time (min.) | | | | Remaining odor | | 20% Index** |
| --- | --- | --- | --- | --- | --- | --- | --- |
| | 5 | 10 | 15 | 20 | Immediately after treatment | 1 day after | |
| 0% | 3.14* | 2.18 | 1.48 | 1.08 | — | — | 0.712 ± 0.013 |
| 0.001% | 0.76 | 0.59 | 0.40 | 0.24 | + | ++ | 0.762 ± 0.011 |

**Average of n = 5,
*Average of n = 5 (ppm)

As is clear form the results shown in Table 1 and FIG. 1, the mercaptan generation amount of methylmercaptan having a rotten-onion like odor was very small, and no substantial remaining odor was detected. The effect of the use of shikonin was also observed in the recovery of hair strength in terms of the 20% index.

EXAMPLE 2

(1) Standard formulation

Waving lotion

Same as in Example 1.

| Neutralizer | |
| --- | --- |
| Composition | % |
| Sodium bromate | 10.0 |
| Potassium phosphate, monobasic | 0.4 |
| Disodium phosphate.12 hydrate, dibasic | 0.3 |
| Cetanol | 0.5 |
| Polyoxyethylene lauryl ether (15 mole EO) | 0.1 |
| Sodium lauryl sulfate | 0.05 |
| Compound (ii) of the present invention listed in Table 2 | 0.05 or 0.1 |
| Purified water | balance |

(2) 20% Index

Determined in the same manner as in Example 1.

(3) Methylmercaptan generation amount and the remaining odor of the permanent waved treated hair when treated with neutralizer Determined in the same manner as in Example 1.

The compounds used in this Example were those slightly soluble in water and, therefore, were formulated into a cetanol type liquid crystal gel base material.

Figure 2:
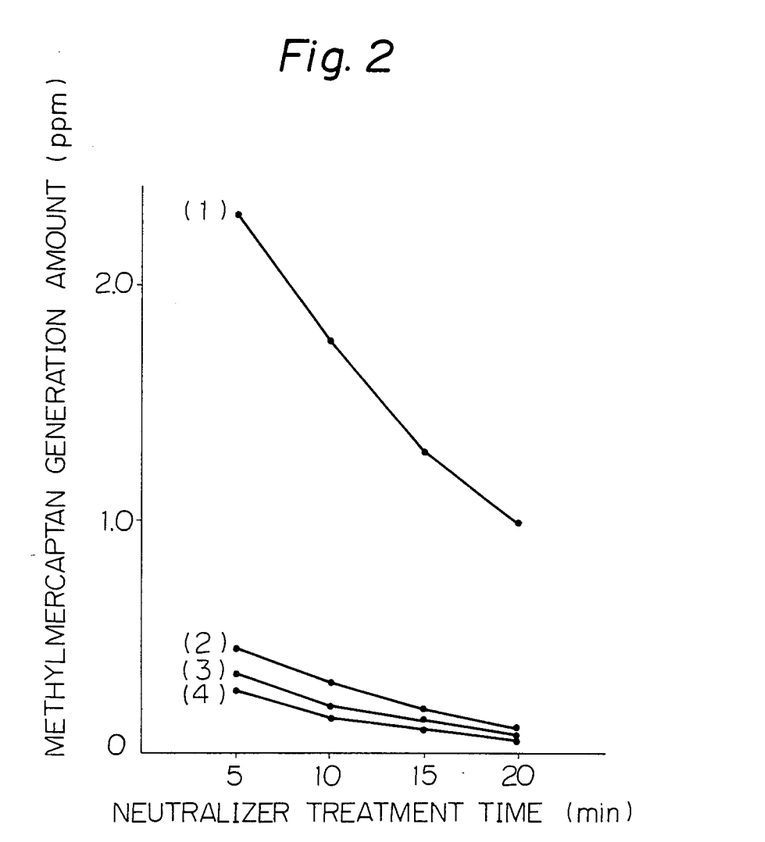
FIG. 2 is a graph illustrating a correlation between a neutralizer treatment time and a methylmercaptan generation amount obtained in Example 2.

The results are shown in Table 2 and FIG. 2. In FIG. 2, the mercaptan generation amounts of Table 2 are shown graphically, in which curve (1) represents the case where there was no addition of compound (ii), and curves (2), (3), and (4) represent the cases where the addition was made of 0.1% of benzyl acetophenone, 0.05% of dibenzyl ketone, and 0.1% of dibenzyl ketone, respectively. As is clearly shown in Table 2 and FIG. 2, an excellent effect was obtained according to the present invention.

Neutralizer

Two types of th neutralizers prepared in Examples 1 and 2 were used. The neutralizers A and B are those prepared in Examples 1 and 2, respectively.

(2) Methylmercaptan generation amount and the remaining odor of permanent waved hair when treated with neutralizer Determined in the same manner as in Examples 1 and 2, except that the quantitative determination of the methylmercaptan was carried out after the 15 minute treatment with the neutralizer.

Typical compounds (ii) according to the present invention listed in Table 3 were formulated into the above-mentioned standard formulation and the odor elimination effect thereof was determined.

The results are shown in Table 3. As is clear from the results shown in Table 1, the neutralizer Nos. 3 to 17 remarkably decrease the remaining mercaptan odor as compared with the comparative neutralizers Nos. 1 and 2.

TABLE 2

Methylmercaptan generation amount, remaining odor, and 20% index when treated with neutralizer

| Compound (ii) in neutralizer | Amount (%) | Treatment time (min) 5 | 10 | 15 | 20 | Remaining odor*** (1 day after) | 20%** Index |
|---|---|---|---|---|---|---|---|
| No addition | — | 2.30* | 1.78 | 1.30 | 1.00 | — | 0.672 |
| Dibenzyl ketone | 0.05 | 0.34 | 0.20 | 0.14 | 0.08 | ++ | 0.730 |
| ⌬—CH₂COCH₂—⌬ | 0.1 | 0.27 | 0.16 | 0.12 | 0.07 | ++ | 0.735 |
| Benzyl acetophenone |  |  |  |  |  |  |  |
| ⌬—COCH₂CH₂—⌬ | 0.1 | 0.45 | 0.30 | 0.19 | 0.11 | ++ | 0.731 |

*, **see Table 1.
***Evaluated in the same manner as in Example 1.

EXAMPLE 3

(1) Standard formulation Waving lotion

Same as in Example 1.

TABLE 3

Odor elimination effect of typical compounds according to the present invention

| No. | General formula | Compound (ii) | Amount | Neutralizer type | Methylmercaptan amount (ppm) | Remaining odor (1 day after) | 20% Index |
|---|---|---|---|---|---|---|---|
| 1 | — | No addition | — | A | 1.48 | — | 0.712 |
| 2 | — | No addition | — | B | 1.30 | — | 0.672 |
| 3 |  | ⌬—CH₂COCH₂—⌬ | 0.05 | B | 0.14 | ++ | 0.730 |
| 4 |  |  | 0.1 | B | 0.12 | ++ | 0.735 |
| 5 | R₁—CO—R₂ | ⌬—COCH₂CH₂—⌬ | 0.1 | B | 0.19 | ++ | 0.731 |

TABLE 3-continued

Odor elimination effect of typical compounds according to the present invention

| No. | General formula | Compound (ii) | Amount | Neutralizer type | Methylmercaptan amount (ppm) | Remaining odor (1 day after) | 20% Index |
|---|---|---|---|---|---|---|---|
| 6 | | C₆H₅-CO-C₆H₅ | 0.1 | B | 0.35 | + | 0.705 |
| 7 | | C₆H₅-CH₂COCH₃ | 1.0 | B | 0.51 | + | 0.723 |
| 8 | | CH₃CO-C₆H₄-COCH₃ | 0.1 | B | 0.21 | ++ | 0.727 |
| 9 | R₄-C₆H₄-COR₆ | NO₂-C₆H₄-COCH₃ | 0.1 | B | 0.19 | ++ | 0.711 |
| 10 | | HO-C₆H₄-COCH₃ | 0.1 | B | 0.26 | + | 0.705 |
| 11 | naphthoquinone-R₇ | 2-hydroxy-1,4-naphthoquinone | 0.01 | A | 0.80 | + | 0.708 |
| 12 | | | 0.05 | | 0.20 | ++ | 0.712 |
| 13 | | | 0.10 | | 0.14 | ++ | — |
| 14 | benzoquinone-(R₇)₂ | 2,5-dihydroxy-1,4-benzoquinone | 0.05 | A | 0.54 | + | — |
| 15 | cyclohexenone-R₆,R₇ | cyclohexenone | 0.05 | A | 0.65 | + | — |
| 16 | | carvone | 0.1 | B | 0.16 | ++ | — |
| 17 | tropone-R₆,R₇ | hinokitiol | 0.05 | A | 0.38 | + | — |

(Remarks) The determination and evaluation methods were the same as in Example 1.

EXAMPLE 4

A waving lotion having the following composition was prepared.

| Composition | % |
|---|---|
| 50% Aqueous ammonium thioglycolate | 12.5 |

-continued

| Composition | % |
|---|---|
| 28% Aqueous ammonia (special reagent grade) | 1.0 |
| Ammonium bicarbonate | 4.0 |
| Tetrasodium EDTA | 0.1 |
| Sodium laury sulfate | 0.1 |
| Purified water | balance |

The above components were mixed at room temperature to prepare the waving lotion.

A neutralizer having the following composition was prepared.

| Composition | % |
|---|---|
| Sodium bromate | 6.0 |
| Potassium phosphate, monobasic | 0.4 |
| Disodium phosphate.12 hydrate, dibasic | 0.3 |
| Sodium lauryl sulfate | 0.1 |
| Polyvinylpyrrolidone-polyvinylstyrene emulsion polymer* | 0.5 |
| Ethyl levulinate | 0.1 |
| Shikonin | 0.001 |
| Propylene glycol | 5.0 |
| Purified water | balance |

*clouding agent (1) Preparatin of neutralizer

Sodium bromate, potassium phosphate, disodium phosphate (12 hydrates), sodium lauryl sulfate, and polyvinylpyrrolidone-polyvinylstyrene emulsion copolymer were added to purified water and these components were dissolved in the water at room temperature while stirring. On the other hand, the shikonin and ethyl levulinate were mixed with the propylene glycol. This mixture was dissolved upon slight heating. The resultant solution was added to the above-prepared mixture, while stirring, to obtain a reddish-purple colored emulsion type neutralizer.

(2) Hair waving test

Hair was wound around rods, while 80 ml of the above-prepared waving lotion was applied to the hair. The remaining amount of the waving lotion was spread over the entire head portion. The hair was allowed to stand for 10 minutes after covering the head portion with a cap.

The hair was washed with slightly warm water and the hair was lightly wipped with a towel to remove excess water. The hair was then treated with 100 ml of the neutralizer by spreading it over the entire head portion. The treated hair was allowed to stand for 15 minutes. Thereafter, the rods were removed and the hair was washed with slightly warm water. The hair was then wiped with a towel to remove excess water.

Good curling of the hair was formed, no unpleasant odor specific to a permanent waving treatment remained in the hair, but a slightly fruity smell was detected.

EXAMPLE 5

A waving lotion having the same composition as in Example 4 was prepared in the same manner as in Example 4.

A neutralizer having the following composition was prepared.

| Composition | % |
|---|---|
| Sodium bromate | 10.0 |
| Potassium phosphate, monobasic | 0.4 |
| Disodium phosphate.12H$_2$O, dibasic | 0.2 |
| Cetanol | 0.5 |
| Polyoxyethylene oleyl ether (20 mol EO) | 0.1 |
| Sodium lauryl sulfate | 0.05 |
| Sodium 1-hydroxyethane-1,1-diphosphonate | 0.1 |
| Dibenzyl ketone | 0.1 |
| Purified water | balance |

(1) Preparation of neutralizer

A 29.35% amount of purified water was heated to about 80° C. and the cetanol, polyoxyethylene oleyl ether, and sodium lauryl sulfate were added thereto. The mixture was stirred in a beaker to form a solution. The resultant solution was water cooled from the outside of the beaker, while gently stirring, to thereby obtain a viscous gel. The dibenzyl ketone was added to the resultant gel and the mixture was uniformly stirred again.

On the other hand, the potassium phosphate, disodium phosphate-12H$_2$O, and sodium 1-hydroxyethane-1,1-diphosphonate were added to the remaining purified water. The mixture was stirred until a clear solution was obtained. The above-prepared part was added to the resultant clear solution and was mixed while stirring to obtain a white milky neutralizer.

(2) Hair waving test

The hair was treated with the above-prepared waving lotion and neutralizer is the same manner as in Example 4.

As a result, good curling of the hair was formed, and no unpleasant odor specific to the permanent waving treatment remained in the hair. Only a slightly flowral smell was detected in the hair.

EXAMPLE 6

A waving lotion having the same composition as in Example 4 was prepared in the same manner as in Example 4.

A neutralizer having the following composition was prepared.

| Composition | % |
|---|---|
| Sodium bromate | 6.0 |
| Potassium phosphate, monobasic | 0.4 |
| Disodium phosphate 12H$_2$O, dibasic | 0.05 |
| Lauryl betain | 0.1 |
| Polyvinylpyrrolidone-polyvinylstyrene emulsion polymer | 0.5 |
| 2-hydroxy-1,4-naphthoquinone | 0.1 |
| Trisodium EDTA | 0.1 |
| Purified water | balance |

(1) Preparation of neutralizer

An orange colored emulsion type neutralizer was prepared in the same manner as in Example 4.

(2) Hair waving test

The hair was treated with the above-prepared waving lotion and neutralizer in the same manner as in Example 4.

As a result, good curling of the hair was formed, and no substantial odor was detected in the hair.

EXAMPLE 7

A waving lotion having the following composition was prepared in the same manner as in Example 4.

| Composition | % |
|---|---|
| L-Cystine | 6.0 |
| Monoethanolamine | 2.5 |
| 28% Special reagent grade aqueous ammonia | 1.0 |
| Tetrasodium EDTA | 0.5 |
| Cetanol | 0.5 |
| Polyoxyethylene oleyl ether (15 mole EO) | 0.1 |
| Sodium lauryl sulfate | 0.05 |
| 50% Aqueous ammonium thioglycolate | 0.5 |
| Purified water | balance |

A neutralizer having the following composition was prepared.

| Composition | % |
|---|---|
| Sodium bromate | 6.0 |
| Potassium phosphate, monobasic | 0.4 |
| Disodium phosphate.12H$_2$O, dibasic | 0.1 |
| Sodium lauryl sulfate | 0.1 |
| 2-Cyclohexenone | 0.1 |
| Hinokitiol | 0.03 |
| Purified water | balance |

(1) Preparation of neutralizer

A clear liquid type neutralizer was obtained in the same manner as described in Example 4.

(2) Hair waving test

The hair was treated with the above-prepared waving lotion and neutralizer in the same manner as in Example 4.

As a result, a soft and elastic curling of the hair was formed. Only a slightly fruity smell was detected in the hair, but no substantial mercaptan odor remained.

EXAMPLE 8

A waving lotion having the same composition as in Example 4 was prepared in the same manner as in Example 4.

A neutralizer having the following composition was prepared.

| Composition | % |
|---|---|
| Sodium bromate | 6.0 |
| Potassium phosphate, monobasic | 0.3 |
| Disodium phosphate.12H$_2$O, dibasic | 0.1 |
| Sodium lauryl sulfate | 0.1 |
| p-Diacetyl benzene | 0.1 |
| Shikonin | 0.001 |
| Polyvinylpyrrolidone-polyvinylstyrene copolymer | 0.5 |
| 1,3-Butylene glycol | 1.0 |
| Purified water | balance |

(1) Preparation of neutralizer

The p-diacetyl benzene and shikonin were added to the 1,3-butylene glycol and the mixture was heated to abot 80° C. to form a solution. On the other hand, sodium bromate, potassium phosphate, disodium phosphate·12H$_2$O, sodium lauryl sulfate, and polyvinylpyrrolidone-polyvinylstyrene copolymer were added to the purified water and the mixture was uniformly stirred to form a solution. To the resultant solution, the above-prepared solution was added. The resultant mixture was thoroughly stirred to obtain a reddish purple colored cloudy neutralizer.

(2) Hair waving test

The hair was treated with the above-prepared waving lotion and neutralizer in the same manner as in Example 4.

As a result, good curling of the hair was formed and no mercaptan odor remained in the hair.

We claim:

1. In an aqueous neutralizer for cold waving comprising 0.5% to 20% by weight of (i) an oxidizing agent, the improvement which comprises incorporating, into the neutralizer, 0.0001% to 5.0% by weight of (ii) at least one compound selected from the group consisting of dibenzyl ketone, p-diacetyl benzene, 2-hydroxy-1,4-naphthoquinone, hinokitiol, shikonin, benzyl acetophenone, p-nitroacetophenone, p-hydroxyacetophenone, benzophenone, 2,5-dihydroxy-1,4-benzoquinone, 2-cyclohexenone, and ethyllevulinate.

2. An aqueous neutralizer as claimed in claim 1, wherein the oxidizing agent is at least one member selected from the group consisting of sodium bromate, hydrogen peroxide, postassium bromate, sodium percarbonate, and sodium perborate.

3. In the waving of hair wherein a waving solution is applied to the hair followed by a neutralizer, the improvement which comprises employing as the neutralizer an aqueous neutralizer according to claim 1.

* * * * *